United States Patent [19]

Pflaumer

[11] 4,244,059
[45] Jan. 13, 1981

[54] NETHER GARMENT FOR AND METHOD OF CONTROLLING CROTCH ODORS

[75] Inventor: Phillip F. Pflaumer, Cincinnati, Ohio

[73] Assignee: The Procter & Gamble Company, Cincinnati, Ohio

[21] Appl. No.: 32,618

[22] Filed: Apr. 23, 1979

Related U.S. Application Data

[63] Continuation of Ser. No. 582,531, May 30, 1975, abandoned.

[51] Int. Cl.³ .............................................. A41B 9/04
[52] U.S. Cl. .......................................... 2/400; 2/406; 424/65; 424/76; 427/332
[58] Field of Search .................... 2/400, 239, 403, 404, 2/406, 407, 409, 53; 427/332; 424/76, 65

[56] References Cited

U.S. PATENT DOCUMENTS

| 2,023,253 | 12/1935 | Stein et al. | 2/53 X |
| 3,027,270 | 3/1962 | Cotton et al. | 427/332 |
| 3,100,159 | 8/1963 | Ullman | 427/332 |
| 3,922,723 | 12/1975 | Popper | 2/406 X |
| 3,971,373 | 7/1976 | Braun . | |

FOREIGN PATENT DOCUMENTS 991203  6/1951  France ........................................ 2/409

Primary Examiner—H. Hampton Hunter
Attorney, Agent, or Firm—Monte D. Witte; Richard C. Witte; John V. Gorman

[57] ABSTRACT

Panty, panty brief, brief or other nether garment provided with a soft, nonbunching air permeable crotch panel provided with means for absorbing odorous molecules from ventilating air passing therethrough and a method of controlling the emission of odors from a woman's crotch region thereby.

9 Claims, 1 Drawing Figure

U.S. Patent
Jan. 13, 1981
4,244,059
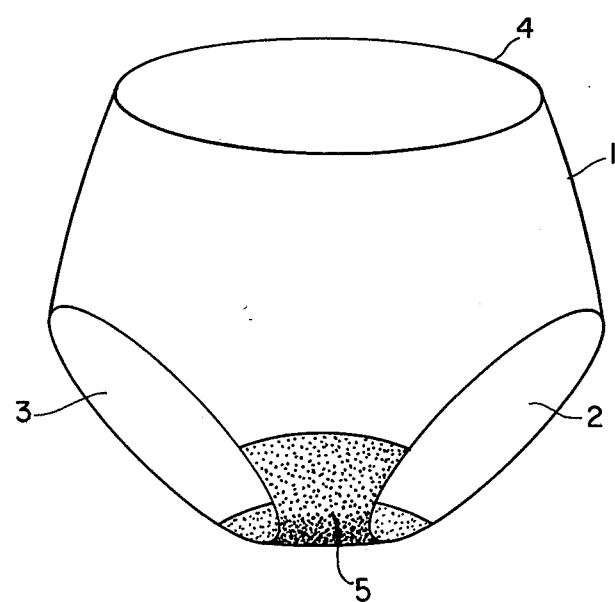

NETHER GARMENT FOR AND METHOD OF CONTROLLING CROTCH ODORS

This is a continuation of application Ser. No. 582,531, filed May 30, 1975 now abandoned.

FIELD OF THE INVENTION

This invention relates to women's nether garments and to the control of crotch odors thereby.

BACKGROUND OF THE INVENTION

Interview studies have indicated that some women are bothered by the emission of odor from their crotch region and particularly by the emission of vaginal odors which may be particularly noticeable during menstruation but which may be present at other times. A variety of measures have been suggested to control these odors, by the use of douches and by the use of deodorizing compounds applied, either internally or externally, to the body tissues or contained within tampons or sanitary pads for deodorizing body secretions themselves or preventing their breakdown or conversion to form odorous gas molecules. It has also been suggested to mask such odors, as by the use of perfumes, or the like.

Each of such previously suggested methods and means for odor control in the crotch region, however, requires either tampering with the normal body chemistry, as by douching or the application of deodorizing substances directly to bodily tissues, or the presence of an absorbent pad structure for absorbing body secretions and providing a chemical reaction with the absorbed secretions within the absorbent body while preventing normal ventilation of the crotch region. Masking the odors with perfumes, or the like, has other obvious disadvantages. Moreover, as has also been recognized, odors may be present at times other than menstruation and with the exception of the direct application of deodorizing compounds to the highly sensitive bodily tissues in the crotch region, whose presence could lead to further chemical imbalance and the continued production of objectionable odors, such nonmenstrual period odors have not heretofore been subject to control.

OBJECTS OF THE INVENTION

Bearing in mind the foregoing, it is a primary object of the present invention to provide novel means for and methods of control of crotch odors.

Another primary object of the present invention, in addition to the foregoing object, is the provision of such means and methods of odor control without the direct application of chemical substances to bodily tissues while permitting ventilation of the crotch region.

Another primary object of the present invention, in addition to each of the foregoing objects, is the provision of a panty, panty brief, brief or other nether garment provided with an air porous crotch panel or structure constructed and arranged to absorb odorous molecules from ventilating air passing therethrough and methods of crotch odor control thereby.

Yet still another primary object of the present invention, in addition to each of the foregoing objects, is the provision of such nether garment crotch structures comprising a porous fabric treated or coated with a carbonate or bicarbonate compound, applied, for example, in an aqueous solution and subsequently dried, and of methods of odor control thereby.

The invention resides in the combination, construction, arrangement and disposition of the various component parts incorporated in new and improved nether garments and in methods of odor control thereby in accordance with the principles of this invention. The present invention will be better understood and objects and important features other than those specifically enumerated above will become apparent when consideration is given to the following details and description which describes and discloses certain preferred embodiments or modifications of the present invention and what is presently considered and believed to be the best mode of practicing the principles thereof. Other embodiments or modifications may be suggested to those having the benefit of the teachings herein, and such other embodiments or modifications are intended to be reserved, especially as they fall within the scope and spirit of the subjoined claims.

BRIEF DESCRIPTION OF DRAWING

The single FIGURE of the drawing shows schematically a panty of this invention.

DETAILED DESCRIPTION OF THE INVENTION

In accordance with the present invention a crotch panel for incorporation into a panty, panty brief, brief or other nether garment is fabricated of a soft, non-bunching, air porous fabric treated with an odor absorbing compound, particularly a bicarbonate compound by add on of about 5 to 20% by weight of the bicarbonate compound, as in aqueous solution, subsequently dried. The resultant crotch panel enables ventilation of the wearer's crotch region while adsorbing acidic and basic odorous molecules from the ventilating air.

The crotch structure may be made of one or a plurality of layers with the crotch structure preferably having an air permeability of at least about 100 cubic feet per square foot per minute at one-half inch water pressure drop. Preferably the porosity is achieved by many small passages through the structure, rather than through a few larger holes as may be typical of apertured nonwoven fabrics. The cotton tricot knits commonly used to make women's panties exemplify the kind of porosity desired.

Preferably the crotch structure comprises absorbent cellulosic fibers and may, for example, comprise a cotton knit cloth or a rayon, nonapertured nonwoven fabric, with a basis weight ranging from about 50 grams per square meter to about 200 grams per square meter.

The crotch panel structure is treated, in accordance with the present invention, by depositing at least about 5% and not more than about 20%, by weight of a bicarbonate, such as sodium bicarbonate or potassium bicarbonate in an aqueous solution and subsequently evaporating the water. The bicarbonate, deposited over the surface of the cellulosic fibers in this way, will adsorb acidic and basic odorous molecules which are the major components of crotch odors from air passing therepast while yet permitting the flow of ventillating air through the crotch panel.

Sodium carbonate and potassium carbonate will also provide the desired odor control but are less desirable because of their high pH. Preferably, about 10% by weight of sodium bicarbonate or potassium bicarbonate is utilized. Polyamine compounds, for example, those derived from ethylenimine also provide a suitable adsorbent coating for use in the present invention.

The crotch panel of the present invention, coated with the odor adsorbent agent may be applied as a separate layer overlying the crotch panel of a conventional garment or may be utilized as the sole crotch structure.

As pointed out above, the crotch structure of the present invention is permeable to air and treated with a material which adsorbs and eliminates the crotch odors from the air passing through it, thus providing an easy and effective means of control without any of the disadvantages of the prior art deodorants, douches or deodorizing absorbent pads and tampons.

The single FIGURE of the drawing shows schematically a panty indicated generally by reference numeral 1. Reference numerals 2 and 3 indicate generally the leg opening portions of the panty and 4 the hip encircling garment support structure portion. Reference numerical 5 indicates the air permeable crotch region portion of the panty which is treated in accordance with this invention.

EXAMPLE I

A sheet of 100% cotton tricot knit fabric such as is conventionally utilized in men's T-shirts was washed at 100° F. in 0 grain demineralized water to remove any sizing therefrom and dried in a conventional tumble type laundry dryer. After drying, the sheet of fabric had a weight of approximately 122 grams.

An 8% sodium bicarbonate solution was prepared and the desized, dried sheet of cotton cloth was immersed therein and wrung out by hand to a total weight of 312 grams, for an add on weight of 190 grams of 8% sodium bicarbonate solution. The cloth was then thoroughly dried, and weighed, and it was found that approximately 12 grams of sodium bicarbonate had been added, an add on weight of approximately 10%.

A crotch inset panel was cut from the dried, bicarbonate treated cloth. This crotch insert panel was then sewn into a legless panty brief.

Women wearing the completed garment reported that the crotch structure was cool and comfortable, provided adequate venting of the crotch region, and effectively prevented the transmission of crotch odors therethrough.

EXAMPLE II

A sample of cotton knit with a basic weight of 118 grams per square meter was desized by washing with a laundry detergent in deionized water in a washing machine, rinsed 3 times in deionized water and dried in a drier. After washing the basis weight was 150.5 grams per square meter.

Ten grams of Tydex-12, made by Dow Chemical Company, a polyamine derived from polyethylenimine was dissolved in 90 grams of water and was added to samples of the cotton fabric described above to provide the additive levels listed in Table I. The samples were dried and then tested in an in vitro odor control test which comprises passing of a metered stream of air past a pool of odorous material such as, for example, butyric acid, a short drawn fatty acid typical of a major component of crotch odors, whereby the air acquires the odor and subsequently passing this odorous air stream through a sample of the test fabric. The air flow rate is increased until a human judge can detect the odor in the air stream passing through the cloth. This "breakthrough flow rate" gives an indication of the ability of the test sample to absorb the odor.

Untreated cloth or ineffective treatments will permit the odor to be passed through and detected by the judge at very low flow rates. On the other hand, effective treatments increase the cloth's absorbency of the odor so that high flow rates are attained before the odor is detected. The results were as shown in the table below.

TABLE I

|  | Sample A | Sample B | Sample C |
| --- | --- | --- | --- |
| % Tydex 12 on Fabric | 13.8 | 9.7 | 5.1 |
| Average air flow ML/min. | 80 | 76.5 | 29 |

EXAMPLE II

A sample of cotton knit fabirc was desized by washing in an aqueous solution of household detergent, rinsed in deionized water and dried as described in Example II. This fabric was then treated by deposition of aqueous solution of the various materials as shown in the following table. The fabrics were dried and tested by the in vitro test method described in Example II. The results of this test are also shown in Table II, demonstrated that sodium chloride and calcium chloride were relatively ineffective and unit sodium carbonate and sodium bicarbonate were relatively more effective.

TABLE II

| Coating Material | % Material on Fabric | Break Thru Flow Rate ML/min. |
| --- | --- | --- |
| NaCl | 28 | 20 |
| $CaCl_2$ | 33 | 24 |
| $Na_2CO_3$ | 8.8 | 90 |
| $NaHCO_3$ | 11.9 | 100 |

It was accordingly demonstrated that the odors which are a cause of concern could be effectively controlled by deodorizing the air which is ventilated through porous panties during normal body movement. The crotch structure as described and disclosed above permits ventilation to occur and coating the fibers with an adsorbent material effectively deodorized the air passing therethrough.

While the invention has been described and disclosed in terms of certain embodiments or modifications herein described and disclosed, such other embodiments or modifications as may be suggested to those having the benefit of the teachings herein are intended to be reserved especially as they fall within the scope and breadth of the claims herein appended.

Having thus described my invention, what I claim is:

1. Panty type garment comprising a crotch panel consisting of a soft fabric having relatively uniform small passages providing an air permeability of at least about 100 cubic feet per square foot per minute at ½ inch $H_2O$ pressure drop and having an odor absorbent compound applied thereto together with hip encircling garment support structure for suspending said crotch panel across a woman's crotch region to permit ventilation thereof while absorbing odors from the ventilating air, wherein said compound is selected from the group consisting of alkali metal bicarbonates, alkali metal carbonates, water soluble polyamines derived from ethylenimine, and mixtures thereof.

2. Panty defined in claim 1 wherein said fabric comprises cellulosic fibers.

3. Panty defined in claim 1 wherein said fabric is selected from the group consisting of cotton and rayon cloths having a basis weight ranging from about 50 to about 200 grams per square meter.

4. Panty defined in claim 1 wherein said odor absorbent compound is applied to the fabric in an aqueous solution, and subsequently dried.

5. Panty defined in claim 4 wherein said compound comprises an add on deposit equal to between about 5% and about 20% by weight, of the weight of the fabric.

6. Panty defined in claim 5 wherein said compound comprises about 10% by weight added on the fabric.

7. Panty defined in claim 6 wherein said compound is an alkali metal carbonate.

8. Panty defined in claim 6 wherein said compound is an alkali metal bicarbonate.

9. Panty defined in claim 1 wherein said odor absorbing compound is a polyamine derived from ethylenimine.

* * * * *